(12) United States Patent
Zielinska et al.

(10) Patent No.: US 8,697,423 B2
(45) Date of Patent: Apr. 15, 2014

(54) **STRAIN OF *LACTOBACILLUS PLANTARUM* S, THE USE OF THE STRAIN OF *LACTOBACILLUS PLANTARUM* S AND THE PREPARATION FOR ROUGHAGES ENSILING**

(71) Applicant: Instytut Biotechnologii Przemyslu Rolno-Spozywczego, Warsaw (PL)

(72) Inventors: Krystyna Zielinska, Warsaw (PL); Krystyna Stecka, Warsaw (PL); Antoni Miecznikowski, Warsaw (PL); Agata Kapturowska, Plock (PL); Marta Kuprys, Biala Podlaska (PL)

(73) Assignee: Instytut Biotechnologii Przemyslu Rolno-Spozywzego, Warszawa (PL)

( * ) Notice: Subject to any disclaimer, the term of this patent is extended or adjusted under 35 U.S.C. 154(b) by 0 days.

(21) Appl. No.: 13/684,983

(22) Filed: Nov. 26, 2012

(65) Prior Publication Data
US 2013/0084623 A1    Apr. 4, 2013

Related U.S. Application Data

(63) Continuation-in-part of application No. PCT/PL2011/000059, filed on Jun. 14, 2011.

(30) Foreign Application Priority Data

Jun. 16, 2010    (PL) .......................................... 391534

(51) Int. Cl.
*C12N 1/20*    (2006.01)
(52) U.S. Cl.
USPC ...................................................... 435/252.9
(58) Field of Classification Search
None
See application file for complete search history.

(56) References Cited

U.S. PATENT DOCUMENTS 4,842,871 A    6/1989    Hill

FOREIGN PATENT DOCUMENTS

EP    1 386 543    2/2004
WO    WO 2010/017568    2/2010

OTHER PUBLICATIONS

Suterska, A.M., Zielinska, K.J., Grzybowski, R.A., Stecka, K.M., Miecznikowski, A.H., and Kuprys, M.P. "Effect of the Selected Strains from *Lactobacillus* Genus on the Limitation of Mould and Ochratoxin A Contamination of Silages from Meadow Sward", Journal of Research and Applications in Agricultural Engineering, Jan. 2009, vol. 53, pp. 125-130.*
Linders, L.J.M., de Jong, G.I.W., Meerdink, G., and van't Riet, K. "Carbohydrates and the Dehydration Inactivation of *Lactobucillus phturum*: The Role of Moisture Distribution and Water Activity", Journal of Food Engineering 1997, vol. 31, pp. 237-250.*
Surjushe, A., Vasani, R., and Saple, D.G. "Aloe Vera: A Short Review", Indian Journal of Dermatology 2008, vol. 53, pp. 163-166.*
Malgorzata Piotrowska, et al., The Elimination of Ochratoxin A by Lactic Acid Bacteria Strains, Polish Journal of Microbiology (2005) vol. 54, No. 4, 279-286.

* cited by examiner

*Primary Examiner* — Allison Ford
*Assistant Examiner* — Michelle F Paguio Frising
(74) *Attorney, Agent, or Firm* — Vedder Price P.C.; Thomas J. Kowalski; Deborah L. Lu

(57) ABSTRACT

The invention relates to the new, genetically non-modified bacterial strain *Lactobacillus plantarum* S, which has been deposited in the IAFB Collection of Industrial Microorganisms Institute of Agricultural and Food Biotechnology in Warsaw under the number KKP 2021 p or variant thereof. The invention relates to use of the strain *Lactobacillus plantarum* S KKP 2021 p or variant thereof or composition which may comprise thereof for ensiling of roughages, with the intention to decontaminate the feeds, contaminated with ochratoxin A, molds and pathogenic bacteria. The feeds contaminated with molds, ochratoxin A and pathogenic microorganisms, after the process of lactic fermentation with the participation of bacteria of the new strain *Lactobacillus plantarum* S, may be employed in nutrition of breeding animals as being completely safe products.

15 Claims, 2 Drawing Sheets

STRAIN OF *LACTOBACILLUS PLANTARUM* S, THE USE OF THE STRAIN OF *LACTOBACILLUS PLANTARUM* S AND THE PREPARATION FOR ROUGHAGES ENSILING

RELATED APPLICATIONS AND INCORPORATION BY REFERENCE

This application is a continuation-in-part application of international patent application Serial No. PCT/PL2011/000059 filed 14 Jun. 2011, which published as PCT Publication No. WO 2011/159178 on 22 Dec. 2011, which claims benefit of Polish patent application Serial No. PL391534 filed 16 Jun. 2010.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The subject of the invention is a new strain of *Lactobacillus plantarum* S bacteria, its use and the preparation for ensiling of contaminated roughages.

BACKGROUND OF THE INVENTION

Ochratoxin A (OTA) is synthesized by moulds from *Aspergillus* sp. and *Penicillium* sp., which are often developed on agricultural products. OTA has been classified by the International Agency for Research on Cancer as carcinogenic factor of category 2B. The monitoring studies, as conducted in different years and concerning OTA presence in feedstuffs and food, indicate the existence of serious hazards for animals and humans, especially during hot and wet years, being favorable for growth of moulds.

From the patent specifications WO 91/13555 and WO 92/05706 methods of binding the mycotoxins in feedstuffs and digestive tract of animals by mineral compounds are known. Use of the mentioned adsorbents bind also water as well as dissolved in water and important for organisms nutrients and vitamins. It is technically impossible to employ the currently known chemical and physical methods of decontamination of the feed, contaminated with OTA directly in agricultural farms, or they are not admitted to application in the EU countries. For that reason biological methods for fodder decontamination, which are based on the application of the selected strains of bacteria and/or yeasts, are demanded.

In the patent specification of US 2004/0208956 A1 following strains of microorganisms are mentioned: *Shingomonas, Stenotrophomonas, Ochrabactrum, Ralstonia* and/or *Eubacterium* and yeasts: *Trichosporon, Cryptococcus* and *Rhodotorula*. These microorganisms are capable of ochratoxins detoxification by enzymatic cleaving of phenylalanine.

Naturally living in the environment and not being genetically modified new strains of lactic acid bacteria might be employed for the improvement of safety of ensiled feeds and in consequence of food. This has become the subject of constantly undertaken studies. The discussed abilities are strictly connected with the specified strains of lactic acid bacteria and cannot be identified with any species or genus of lactic acid bacteria. The mentioned group of microorganisms contains in numerous bacterial strains which are characterized—to a different extent—by the ability to lower OTA content in the model environment. On the other hand, there is a lack of the results of their practical application for decontamination of OTA-infected feeds, especially in the manufacturing conditions of agricultural farms.

It is impossible to protect the agricultural products from contamination with toxin-producing moulds. For that reason simple biological methods for eliminating or reducing OTA content by the selected bacterial strains from *Lactobacillus* sp. with GRAS status are being searched. These bacteria might be employed as starter cultures in the process of feed ensiling.

Citation or identification of any document in this application is not an admission that such document is available as prior art to the present invention.

SUMMARY OF THE INVENTION

The purpose of the invention was to select a strain of lactic acid bacteria, characterized by the ability of growing in the environment contaminated with ochratoxin A and reducing OTA level by at least 80% in order to apply it in ensiling of the contaminated roughages.

The strain according to the invention, was isolated from the spontaneous fermentating maize plants. It was classified to *Lactobacillus plantarum* species on the basis of studying morphological and physiological-biochemical properties with API 50 CH kit (Biomerieux, France) and selected in order to obtain the ability of developing and synthesizing organic acids in growth media, containing ochratoxin A in concentration of 50-100 ppb.

The object of the invention is the new bacterial strain, which was specified as *Lactobacillus plantarum* S and deposited in the IAFB Collection of Industrial Microorganisms Institute of Agricultural and Food Biotechnology in Warsaw under the number KKP 2021 p or variant thereof.

The second object of the invention is the composition which may comprise an effective amount of *Lactobacillus plantarum* S deposited under the number KKP 2021 p or variant thereof. Preferred composition further may comprise at least one carrier and/or at least one emulsifier and/or at least bio-stimulator, preferably is in dry form The third object of the invention includes granular or powder preparation for ensiling of the roughages which contains dried-on-the carrier biomass of *Lactobacillus plantarum* S KKP 2021 p with bacterial number equal to 9-10 log CFU/g of the preparation; the composition of the carriers contains extract from aloes which constitutes 0.2-2.0% of dry matter of the preparation.

Another object of the invention is a method of ensiling of roughages, which may comprise the step of ensiling of roughages with use of new strain of *Lactobacillus plantarum* S KKP 2021 p according to the invention and/or the composition according to the invention and/or preparation according to the invention.

Another object of the invention is the use of the new strain of *Lactobacillus plantarum* S KKP 2021 p or variant thereof for ensiling of roughages, intended for decontamination of roughages, contaminated with ochratoxin A and/or moulds and/or with pathogenic bacteria selected from genus *Salmo-* nella and/or genus *Listeria* and/or coliform bacteria and/or bacteria of the species *Escherichia coli* and/or *Clostridium perfringens*.

Another object of the invention is the use of new strain of *Lactobacillus plantarum* S KKP 2021 p according to the invention and/or the composition according to the invention and/or preparation according to the invention for ensiling of roughages. Preferably ensiling of roughages is carried out to decontaminate or/and restrain from contamination and/or prevent contamination of roughages, contaminated with ochratoxin A and/or moulds and/or with pathogenic bacteria selected from genus *Salmonella* and/or genus *Listeria* and/or coliform bacteria and/or bacteria of the species *Escherichia coli* and/or *Clostridium perfringens*.

By the term variant of new strain *Lactobacillus plantarum* S KKP 2021 p it should be understood the mutant strain or strains obtained by rising the deposited strain as starter material, wherein the mutant strain(s) retain or further improve the ability of growing and activity of parent strain i.e. ability to grow in the environment contaminated with ochratoxin A and reducing OTA level and/or reducing moulds and/or reducing pathogenic bacteria growth.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

The Deposits with International Collection of Industrial Microorganism Cultures of the Institute of Agricultural and Food Biotechnology, under deposit accession number KKP 2021 p were made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings. For a better understanding of the invention it will be described by the way of example only with reference to the accompanying drawings in which.

DETAILED DESCRIPTION OF THE INVENTION

The new strain according to the invention, was isolated from the spontaneous fermentating maize plants. It was classified to *Lactobacillus plantarum* and deposited in the International Collection of Industrial Microorganism Cultures of the Institute of Agricultural and Food Biotechnology under the number KKP 2021 p.

*Lactobacillus plantarum* S KKP 2021 p strain is characterized by the following features:
  morphological—it creates colonies of the white to creamy colour, with a shape of discs of the size of 0.5-0.7 mm. Bacterial cells have a form of short rods occurring singly, in pairs or in chains of 0.9-1.2 µm. They do not produce spores and are Gram+.
  physiological and biochemical—the optimal temperature of growth is 30° C. The new strain is relatively heterofermentative, microaerophilic, does not produce catalase, does not reduce nitrates to nitrites, and is capable of fermenting the following sugars: saccharose, galactose, glucose, fructose, arabinose, maltose, mannose, esculin, lactose, cellobiose, gentiobiose, mellibiose, rafinose, ribose, xylose, sorbitol and trehalose.

Genetic analysis of the sequence of 16S rDNA segments and their comparison with sequences of bacterial 16S rDNA segment, deposited in the GenBank base, confirmed in 98% the taxonomic affiliation of the examined strain to *Lactobacillus plantarum* species, specified by biochemical properties. Genetic analysis involved a technique of molecular fingerprinting—RAPD-PCR based on randomly amplified polymorphic regions of genomic DNA. PCR reaction was carried out using the following primer: 5' GAGGGTGGCG-GTTCT 3' and amplification conditions according to Andrighetto et. al. 2001 (Lett. Appl. Microbiol. 33, 26-30).

The sequence of 16S rDNA segment of *Lactobacillus plantarum* S KKP 2021 p is given on SEQ ID NO:1.

The new strain is characterized by the ability of developing and synthesizing lactic acid in medium, containing ochratoxin A and of removing it from the environment in at least 80% as well as inhibiting growth of moulds. Moreover, it was revealed that the new strain showed, simultaneously, a very high antibacterial activity against pathogenic bacteria from *Salmonella* and *Listeria* genus, *Escherichia coli* and *Clostridium perfringens*, which are often present in agricultural products, cultivated on organically fertilized land, especially with the use of liquid organic manure.

Figure 1:
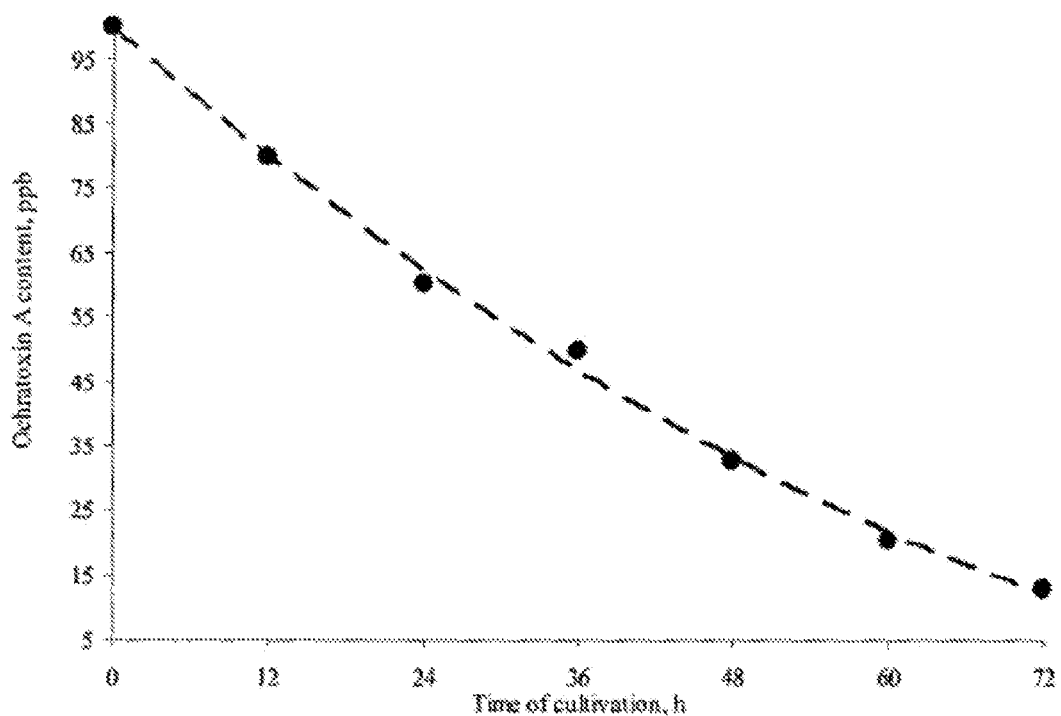
FIG. 1 shows changes in ochratoxin A content in medium during cultivation of *Lactobacillus plantarum* S KKP 2021 p and FIG. 2 shows survival of pathogenic bacteria during their incubation with the strain *Lactobacillus plantarum* S KKP 2021 p.

Cultivation of the new strain *Lactobacillus plantarum* S KKP 2021 p under model conditions in MRS medium at temperature of 30° C. for 72 h resulted in reducing the content of ochratoxin A by 87.2% in relation to its initial level (see FIG. 1).

Antibacterial activity of the strain *Lactobacillus plantarum* S KKP 2021 p in relation to pathogenic strains: *Salmonella* sp. and *Escherichia coli*, isolated from digestive tract of sick animals was determined by Pilet method (Pilet et al., 1995, J.

Food Prot., 58, 256-262). After 24 hours of cultivation of the examined strain, 10 μl of supernatant were introduced onto the surface of agar medium with the diameter of 10 cm, containing *Salmonella* sp. or *Escherichia coli*. After the successive 24 hours, the diameter of bacterial growth inhibition zone was measured. In the experimental conditions metabolites, produced by the strain *Lactobacillus plantarum* S KKP 2021 p, inhibited the growth of tested pathogenic bacteria in the range of 90-100%.

During 7 days of incubation, the survivability of the cultures of *Salmonella* sp. and *Escherichia coli* bacteria were evaluated.

Figure 2:
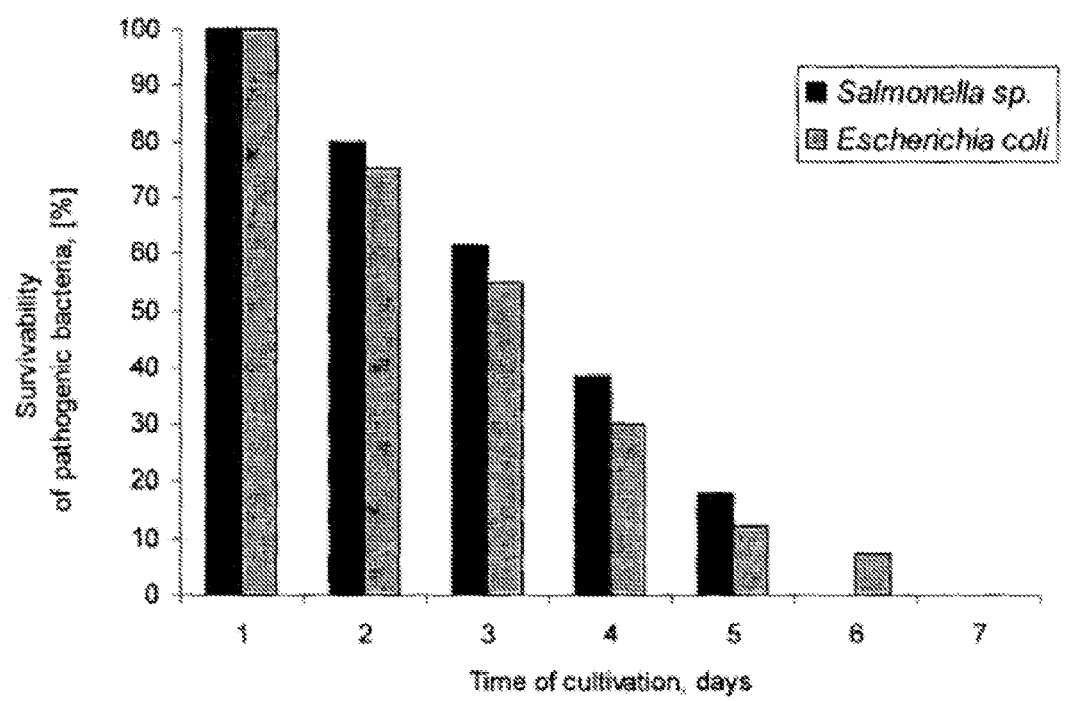

Bacterial cultures cultivated for 24 h were employed as the experimental material. The cultures of *Salmonella* sp. and *Escherichia coli*, with the number of bacteria 6.5 and 6.0 log CFU/ml, respectively, were combined with the culture of *Lactobacillus plantarum* S KKP 2021 p bacteria with the number of bacteria 9.0 log CFU/ml in v/v ratio 1:1. After six days of incubation, the new strain *Lactobacillus plantarum* S KKP 2021 p inhibited completely *Salmonella* sp. growth and after seven days of incubation—development of *Escherichia coli* (see FIG. 2).

Although the present invention and its advantages have been described in detail, it should be understood that various changes, substitutions and alterations can be made herein without departing from the spirit and scope of the invention as defined in the appended claims.

The present invention will be further illustrated in the following examples which are given for illustration purposes only and are not intended to limit the invention in any way.

EXAMPLES

Example 1

Cultivation of biomass of *Lactobacillus plantarum* S KKP 2021 p was conducted in fermentors with volume of 150 l, at temperature of 30° C., at pH 5.7, regulated by ammonia water. The content of the components of culture medium in g/l water was as follows: glucose—20, yeast extract—10, maize soak—5, ammonium biphosphate—0.2, ammonium sulphate—0.35 and manganese sulphate—0.01. Bacteria were cultivated for 24 h. Bacteria biomass with ca. 30% DM, obtained after separation of culture medium at rotations of separator equal to 14000/min., was mixed with the following carriers: mix of starter sugars: saccharose, glucose, lactose, soluble potato starch, emulsifier (lecithin) and bio-stimulator (aloes extract). Then, it was dried in fluidal drier at temperature up to 40° C. The dried bacterial preparation contained ca. 94% DM, including: 90% sugars; 0.2% of dried aloes extract and 3.8% of dried bacterial biomass and was characterized by the number of bacteria equal to 9.0 log CFU/g (colonies-forming units).

Example 2

In the experimental agricultural farm, two types of silages were produced: from meadow sward and maize plants with humidity of ca. 40%, contaminated with ochratoxin A, moulds and pathogenic bacteria. To obtain the experimental silages, the preparation, according to the invention (obtained in example I), in the rate of 10 g/t of the cut green forage, was applied in a form of water spray. After six weeks and completion of ensiling process, the samples of silages without and with the addition of the preparation were collected. The influence of *Lactobacillus plantarum* S KKP 2021 p on reduction of ochratoxin A, number of moulds and pathogenic bacteria in the ensiled feedstuffs were examined. In the experimental silages with the addition of the preparation, the content of ochratoxin A in maize plants was lowered from 30.6 ppb to 4.5 ppb (85.3%); and in meadow sward—from 25.5 ppb to the level of 3.2 ppb (87.4%). In the silages, produced without the addition of the preparation, the content of ochratoxin A was lowered by 6.7-7.5%, depending on the initial concentration and type of the ensiled plants (Table 1)

TABLE 1

Effect of the preparation on reduction of the content of ochratoxin A during the process of the roughages ensiling

| Type of feedstuff and/or silage with DM ca. 40% | Content of ochratoxin A, ppb | The remaining content, % |
| --- | --- | --- |
| Meadow sward - green forage | 25.5 | 100.0 |
| Meadow sward - silage A | 23.8 | 93.3 |
| Meadow sward - silage B | 3.2 | 12.6 |
| Maize plants - green forage | 30.6 | 100.0 |
| Maize plants - silage A | 28.3 | 92.5 |
| Maize plants - silage B | 4.5 | 14.7 |

A—silages without the addition of the preparation
B—silages with the addition of the preparation At the same time, microbiological purity of the silages produced without and with the addition of the preparation was examined; their microbiological contamination with bacteria from genus: *Salmonella* and *Listeria*, species: *Escherichia coli* and *Clostridium perfringens* as well as moulds, was determined. The results concerning the effect of the preparation on the improvement of the state of hygiene of the silages is given in Table 2.

TABLE 2

Microbiological contamination of ensiled roughages without and with the addition of the preparation

| | Number of pathogenic bacteria and moulds in silages, log CFU/g | | | | | |
| --- | --- | --- | --- | --- | --- | --- |
| Type of silage produced from: | *Salmonella* sp. | *Listeria* sp. | *Escherichia coli* | Coliform bacteria | *Clostridium perfringens* | Moulds |
| Meadow sward-A | 2.60 | 3.88 | 3.30 | 2.50 | 3.70 | 5.60 |
| Meadow sward-B | no presence | 1.44 | no presence | no presence | 1.00 | 1.30 |
| Maize plants-A | 2.30 | 3.60 | 2.70 | 3.30 | 2.30 | 5.20 |
| Maize plants-B | no presence | 1.28 | no presence | 1.00 | 0.50 | 1.00 |

A—silages without the addition of the preparation
B—silages with the addition of the preparation In the meadow sward silages produced with the addition of the preparation, pathogenic bacteria from genus *Salmonella* and the species *Escherichia coli* as well as coliform bacteria were eliminated in 100%. In the silages produced from maize plants with the addition of the preparation, the presence of *Salmonella* sp. and *Escherichia coli* were not found and coliform bacteria constituted only 30% of their number contained in the silage expressed in log CFU/g, produced without the preparation. The number of bacteria *Clostridium perfringens* in the silages with the addition of the preparation was lowered by 73 and 78%, respectively, and the number of *Listeria* sp. was lowered by 63 and 64%, respectively. On the other hand, the number of moulds was lowered by 77% in the silages produced from meadow sward and by 80% in the silages from maize plants as compared to the silages obtained without the addition of the preparation *Lactobacillus plantarum* S KKP 2021 p.

The contaminated with ochratoxin A and pathogenic microorganisms feeds, after the process of lactic fermentation provided by bacteria of the new strain *Lactobacillus plantarum* S KKP 2021 p, may be employed as completely safe products in feeding of breeding animals.

The invention is further described by the following numbered paragraphs:

1. The new strain of *Lactobacillus plantarum* S, deposited in the IAFB Collection of Industrial Microorganisms Institute of Agricultural and Food Biotechnology in Warsaw under the number KKP 2021 p or variant thereof.

2. A composition of preparation comprising an effective amount of *Lactobacillus plantarum* S deposited under the number KKP 2021 p or variant thereof.

3. The composition according to paragraph 2, which further comprises at least one carrier and/or at least one emulsifier and/or at least one bio-stimulator.

4. The composition according to paragraph 3, wherein the bacterial biomass comprising *Lactobacillus plantarum* S KKP 2021 p or variant thereof is in dry form.

5. The preparation for ensiling roughages, in a granular form or powder, consisting of dried bacterial biomass and carriers, characterized in that it comprises the strain *Lactobacillus plantarum* S KKP 2021 p with bacterial number of 9-10 log CFU/g and the composition of the carriers contain aloes extract which constitutes 0.2-2.0% of dry matter of the preparation.

6. A method of ensiling of roughages, wherein it comprises the step of ensiling of roughages with use of new strain of *Lactobacillus plantarum* S according to paragraph 1 and/or the composition according to paragraphs 2-4 and/or preparation according to paragraph 5.

7. The use of the new strain of *Lactobacillus plantarum* S KKP 2021 p or variant thereof for ensiling of roughages, intended for decontamination of roughages, contaminated with ochratoxin A and/or moulds and/or with pathogenic bacteria selected from genus *Salmonella* and/or genus *Listeria* and/or coliform bacteria and/or bacteria of the species *Escherichia coli* and/or *Clostridium perfringens*.

8. The use of new strain of *Lactobacillus plantarum* S according to paragraph 1 and/or the composition according to paragraphs 2-4 and/or preparation according to paragraph 5 for ensiling of roughages.

9. The use according to paragraph 8, wherein ensiling of roughages is carried out to decontaminate or/and restrain from contamination and/or prevent contamination of roughages, contaminated with ochratoxin A and/or moulds and/or with pathogenic bacteria selected from genus *Salmonella* and/or genus *Listeria* and/or coliform bacteria and/or bacteria of the species *Escherichia coli* and/or *Clostridium perfringens*.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A biologically pure culture of *Lactobacillus plantarum* S, deposited in the IAFB Collection of Industrial Microorganisms Institute of Agricultural and Food Biotechnology in Warsaw under the number KKP 2021 p.

2. A composition comprising an effective amount of *Lactobacillus plantarum* S for ensiling roughages deposited in the IAFB Collection of Industrial Microorganisms Institute of Agricultural and Food Biotechnology in Warsaw under the number KKP 2021 p.

3. The composition according to claim 2, which further comprises at least one carrier and/or at least one emulsifier and/or at least one bio-stimulator.

4. The composition according to claim 3, wherein the bacterial biomass comprising *Lactobacillus plantarum* S KKP 2021 p is in dry form.

5. A preparation for ensiling roughages, in a granular form or powder, comprising the strain *Lactobacillus plantarum* deposited in the IAFB Collection of Industrial Microorganisms Institute of Agricultural and Food Biotechnology in Warsaw under the number S KKP 2021 p with a bacterial number of 9-10 log CFU/g and an aloe extract which constitutes 0.2-2.0% of dry matter of the preparation.

6. A method of ensiling of roughages, comprising a step of ensiling of roughages with the new strain of *Lactobacillus plantarum* S according to claim 1.

7. The method of claim 6, wherein the method further results in decontamination of roughages, contaminated with ochratoxin A and/or molds and/or with pathogenic bacteria selected from genus *Salmonella* and/or genus *Listeria* and/or coliform bacteria and/or bacteria of the species *Escherichia coli* and/or *Clostridium perfringens*.

8. A method of ensiling of roughages, comprising a step of ensiling of roughages with the composition according to claim 2.

9. The method of claim 8, wherein the method further results in decontamination of roughages, contaminated with ochratoxin A and/or molds and/or with pathogenic bacteria selected from genus *Salmonella* and/or genus *Listeria* and/or coliform bacteria and/or bacteria of the species *Escherichia coli* and/or *Clostridium perfringens*.

10. A method of ensiling of roughages, comprising a step of ensiling of roughages with the composition according to claim 3.

11. The method of claim 10, wherein the method further results in decontamination of roughages, contaminated with ochratoxin A and/or molds and/or with pathogenic bacteria selected from genus *Salmonella* and/or genus *Listeria* and/or coliform bacteria and/or bacteria of the species *Escherichia coli* and/or *Clostridium perfringens*.

12. A method of ensiling of roughages, comprising a step of ensiling of roughages with the composition according to claim 4.

13. The method of claim 12, wherein the method further results in decontamination of roughages, contaminated with ochratoxin A and/or molds and/or with pathogenic bacteria selected from genus *Salmonella* and/or genus *Listeria* and/or coliform bacteria and/or bacteria of the species *Escherichia coli* and/or *Clostridium perfringens*.

14. A method of ensiling of roughages, comprising a step of ensiling of roughages with the preparation according to claim 5.

15. The method of claim 14, wherein the method further results in decontamination of roughages, contaminated with ochratoxin A and/or molds and/or with pathogenic bacteria selected from genus *Salmonella* and/or genus *Listeria* and/or coliform bacteria and/or bacteria of the species *Escherichia coli* and/or *Clostridium perfringens*.

* * * * *

SEQUENCE LISTING

```
<160> NUMBER OF SEQ ID NOS: 1

<210> SEQ ID NO 1
<211> LENGTH: 675
<212> TYPE: DNA
<213> ORGANISM: Lactobacillus plantarum

<400> SEQUENCE: 1
taaaaggtta ccccaccgac tttgggtgtt acaaactctc atggtgtgac gggcggtgtg      60
tacaaggccc gggaacgtat tcaccgcggc atgctgatcc gcgattacta gcgattccga     120
cttcatgcag gcgagttgca gcctgcaatc cgaactgaga atggttttaa gagattagct     180
taccctcgcg agttcgcgac tcgttgtacc atccattgta gcacgtgtgt agcccaggtc     240 ataagggca tgatgatttg acgtcatccc caccttcctc cggtttgtca ccggcagtct     300
caccagagtg cccaacttaa tgctggcaac tgataataag ggttgcgctc gttgcgggac     360
ttaacccaac atctcacgac acgagctgac gacaaccatg caccacctgt attcgtgtcc     420
ccgaagggga acgtctaatc tcttagattg gcataaagat gtcaagacct gggtaaggtt     480
cttcgcgtag cttcgaatta aaccacatgc tccaccgctt gtgcgggccc ccgtcaattc     540
```

-continued

```
cctttgagtt tcaaccttgc ggtcgtactc cccagggcgg agttgcttaa tgcgttagct      600
gcaagcactg aagggcggga aacccctcca accacttagc cactcatcgt ttacggtatg      660
gactaccagg gtatc                                                       675
```